United States Patent [19]
Hansen et al.

[11] Patent Number: 6,063,799
[45] Date of Patent: May 16, 2000

[54] ALTERNATE CRYSTAL FORM OF TAZOFELONE

[75] Inventors: Marvin M Hansen; Allen R Harkness; Susan M Reutzel, all of Indianapolis, Ind.

[73] Assignee: Eli Lilly and Company, Indianapolis, Ind.

[21] Appl. No.: 09/029,205

[22] PCT Filed: Sep. 3, 1996

[86] PCT No.: PCT/US96/14132

§ 371 Date: Feb. 25, 1998

§ 102(e) Date: Feb. 25, 1998

[87] PCT Pub. No.: WO97/09320

PCT Pub. Date: Mar. 13, 1997

[51] Int. Cl.[7] .................. A61K 31/425; C07D 277/04
[52] U.S. Cl. .............................. 514/369; 548/186
[58] Field of Search .................. 548/186; 514/369

[56] References Cited

U.S. PATENT DOCUMENTS

| | | | |
|---|---|---|---|
| 5,216,002 | 6/1993 | Gidda et al. .................. | 514/369 |
| 5,356,917 | 10/1994 | Panetta ........................ | 514/369 |
| 5,387,690 | 2/1995 | Gidda et al. .................. | 548/186 |
| 5,523,314 | 6/1996 | Bue-Valleskey et al. ....... | 514/369 |
| 5,563,277 | 10/1996 | Hansen et al. ................ | 548/182 |

FOREIGN PATENT DOCUMENTS

| | | | |
|---|---|---|---|
| 0 211 670 | 2/1987 | European Pat. Off. | 31/39 |
| 0 391 644 | 10/1990 | European Pat. Off. | 277/14 |
| 0 434 394 | 6/1991 | European Pat. Off. | 277/14 |
| 0 500 337 | 8/1992 | European Pat. Off. | 31/38 |

OTHER PUBLICATIONS

American Chemical Society, 208th ACS National Meeting, Washington, D.C., Aug. 21–25, 1994, #230.

Roberts, et al., *Spectroscopy Letters*, 26 (10), pp. 1901–1921, 1993.

Hansen, et al., *Tetrahedron Letters*, 35 (38), pp. 6971–6974, 1994.

Phillips, et al., *J. Org. Chem.*, 57 (14), pp. 4047–4049, 1992.

*Primary Examiner*—Raymond Henley, III
*Attorney, Agent, or Firm*—Suzanne M. Harvey; Nelsen L. Lentz

[57] ABSTRACT

The instant invention provides novel crystalline Form II of (±)-5-{[3,5-bis(1,1dimethylethyl)-4-hydroxyphenyl]methyl}-4-thiazolidinone having an x-ray powder diffraction patter with specific d spacings useful for treating inflammation, inflammatory bowel disease, allergies, arthritis and hypoglycemia utilizing the novel physical form as well as pharmaceutical compositions containing the same. A process for preparing Form II Tazofelone is described.

9 Claims, No Drawings

ALTERNATE CRYSTAL FORM OF TAZOFELONE

This is a 371 of PCT/US96/14132 filed Sep. 3, 1996.

This invention relates to a novel physical form of (±)-5-{[3,5-bis(1,1-dimethylethyl)-4-hydroxyphenyl]methyl}-4-thiazolidinone useful in the treatment of inflammation, inflammatory bowel disease (hereinafter IBD), allergies, arthritis, hypoglycemia and muscular dystrophy and in preventing ischemia induced cell damage.

Benzyl-substituted rhodanine derivatives are known to be active in treating inflammation, inflammatory bowel disease (hereinafter IBD), allergies, arthritis, hypoglycemia and muscular dystrophy and in preventing ischemia induced cell damage. For example, U.S. Pat. No. 5,216,002 discloses that certain benzyl-substituted rhodanine derivatives are useful for treating IBD. EPO Publication No. 391644, on the other hand, discloses the effectiveness of such compounds for treating inflammation, arthritis, and muscular dystrophy and for preventing ischemia induced cell damage. EPO Publication No. 343643 describes the use of such compounds for treating allergies and inflammation, while EPO Publication No. 587377 discloses these compounds as being effective in treating hypoglycemia.

Tazofelone is a generic term used to identify the chemical compound (±)-5-{[3,5-bis(1,1-dimethylethyl)-4-hydroxyphenyl]methyl}-4-thiazolidinone represented by the structural formula:

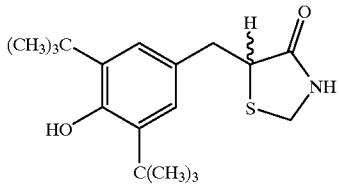

Tazofelone is particularly useful in treating inflammatory bowel diseases (IBD), ulcerative colitis and Chrohn's disease.

Tazofelone has a chiral center and, as such, can exist either as individual stereoisomers or in racemic form. Both the racemate and stereoisomers may be obtained according to procedures well known in the art. as described in U.S. Pat. No. 5,356,917 and U.S. Pat. No. 5,216,002, herein incorporated by reference.

It is desirable to prepare therapeutic agents of uniform and defined composition.

This invention provides a new, substantially pure crystalline form II of (±)-5-{[3,5-bis(1,1-dimethylethyl)-4-hydroxyphenyl]methyl}-4-thiazolidinone having a typical x-ray powder diffraction pattern with characteristic d spacing at 5.64 Å.

The method of this invention also provides a process for producing this substantially pure form II of (±)-5-{[3,5-bis(1,1-dimethylethyl)-4-hydroxyphenyl]methyl}-4-thiazolidinone.

In another embodiment of this invention, there is provided a pharmaceutical formulation containing the substantially pure form II Tazofelone as an active ingredient.

Finally, the present invention provides a method of using the new substantially pure form to prevent and/or treat inflammation, inflammatory bowel disease, allergies, arthritis, hypoglycemia and muscular dystrophy and in preventing ischemia-induced cell damage.

Applicants have discovered that the 5-{[3,5-bis(1,1-dimethylethyl)-4-hydroxyphenyl]methyl}-4-thiazolidinone racemate exists in two different physical forms which are distinguishable by x-ray powder diffractometry, solid-state Nuclear Magnetic Resonance (NMR) or differential scanning calorimetry. The two polymorphic forms of the racemate are hereinafter designated Form I and Form II.

Both forms of Tazofelone are non-solvated and stable indefinitely at room temperature.

Form I is the predominant crystal form at temperatures from about 60° C. to about 155° C. Substantially pure Form I can be obtained in a laboratory setting by refluxing 3,5-di-tert-butyl-4-hydroxybenzaldehyde with rhodanine in glacial acetic acid using fused sodium acetate as a catalyst to form 5-{[3,5-bis(1,1-dimethylethyl)-4-hydroxyphenyl]}-methylene-2-thioxo-4-thiazolidinone. The resultant 2-thioxo-4-thiazolidinone can then be reduced with hydrogen in the presence of palladium on carbon. The product is isolated by chromatography, and the solvent is removed to afford Form I Tazofelone. In an alternate preparation, 5-{[3,5-bis(1,1-dimethylethyl)-4-hydroxyphenyl]}-methylene-2-thioxo-4-thiazolidinone can be refluxed with diethyl 1,4-dihydro-2,6-dimethyl-3,5-pyridinedicarboxylate and activated silica gel to form (±)-5-{[3,5-bis(1,1-dimethylethyl)-4-hydroxyphenyl]-methyl}-2-thioxo-4-thiazolidinone. The methyl-2-thioxo-4-thiazolidinone can then be reduced using hydrogen in the presence of palladium on carbon.

In yet another process, the methyl-2-thioxo-4-thiazolidinone can also be reduced by refluxing with zinc dust in acetic acid.

In still another process for preparing Form I, the methyl-2-thioxo-4-thiazolidinone can be treated with formaldehyde and ammonia in methanol.

Form I has an x-ray powder diffraction pattern with characteristic d spacing at 7.20 Å and a melting point of 155.5° C.

Unfortunately, while substantially pure Form I can be readily obtained in a laboratory setting, it is difficult to isolate at ambient temperatures in large scale production. Furthermore, when Form I is slurried, it has been found to convert to Form II at ambient temperatures. However, surprisingly, and in accordance with the invention, it has now been discovered that substantially pure Form II, is obtainable in a process readily adapted to commercial production.

Form II is more stable than Form I at ambient temperatures and can be obtained by slurrying Form I at 20–60° C., preferably at room temperature, in an organic solvent.

Form II has been found to have a defining x-ray diffraction pattern with characteristic d spacing at 5.64 Å. This physical form is provided as one aspect of the present invention.

The term "substantially pure" as used herein refers to a Form II which preferably contains at least 90 mole percent of the desired Form II being present compared to other polymorphs present. Most preferably, a substantially pure Form II contains at least 95 mole percent of Form II.

Each of Forms I and II have been characterized by x-ray diffraction, by $^{13}C$ solid-state Nuclear Magnetic Resonance (NMR) spectroscopy and by differential scanning calorimetry. The techniques used, and the physical characteristics determined for samples of each Tazofelone form are given below:

Characterization of Forms I and II Tazofelone by NMR $^{13}C$ Cross polarization/magic angle spinning (CP/MAS) NMR spectra (SSNMR) were obtained using a Varian Unity 400 MHz spectrometer operating at a carbon frequency of 100.577 MHz and equipped with a complete solids accessory and Varian 5 mm or 7 mm VT CP/MAS probe. Typical measurement conditions were as follows: 90° proton r.f. pulse 4 μs, contact time 1 ms, pulse repetition time 5 s, MAS frequency 7 kHZ, spectral width 50 kHZ, and acquisition time 50 ms. The chemical shifts were referenced to the $CH_3$ group of hexamethylbenzene (delta=17.3 ppm) by sample replacement.

Form I has characteristic NMR resonances at 132.7, 136.8 and 30.4 ppm.

Form II has characteristic NMR resonances at 133.5 and 135.8 ppm.

TABLE I

| Solid-State $^{13}$C NMR (SSNMR) Form I | Chemical Shift Data Form II |
|---|---|
| 43.3 | 43.8 |
| 181.0 | 180.9, 181.4 |
| 47.7 | 47.2 |
| 39.4 | 39.4 |
| 126.8 | 127.0 |
| 126.3, 128.0 | 127.0, 128.1 |
| 132.7, 136.8 | 133.5, 135.8 |
| 153.3 | 153.2 |
| 33.8, 35.5 | 34.2, 35.3 |
| 30.4, 31.6, 32.4 | 31.7, 32.2 |

Characterization of Forms I and II Tazofelone By Differential Scanning Calorimetry Differential scanning calorimetry (DSC) measurements were performed on a Perkin-Elmer DSC7 differential scanning calorimeter. Samples (1–3 mg) were sealed in aluminum pans and heated from 25 to 175° C. at a rate of 2.5° C./min.

DSC Form I: Endotherm at 155.5° C. ±0.2.
DSC Form II: Endotherm at 154.2° C. ±0.2.

Characterization of Forms I & II Tazofelone by X-Ray Diffraction

X-ray diffraction patterns were obtained on a Nicolet I2 x-Ray powder diffractometer, equipped with a CuKα source λ=1.54056 Å) and a Kevex solid-state detector, and operating at 50 kV and 40 mA. Each sample was scanned between 4 and 35° in 2 θ, with a step size of 0.05° and a scan rate of 3 sec/step.

Form I Tazofelone has the following x-ray powder diffraction pattern, wherein d represents the interplanar spacing and $I/I_o$ the relative intensity:

| Spacing d(Å) | Relative Intensity $I/I_O$ |
|---|---|
| 7.20 | 5 |
| 4.84 | 33 |
| 4.76 | 24 |

The new purified Form II Tazofelone has the following x-ray powder diffraction pattern, wherein d represents the interplanar spacing and $I/I_o$ the relative intensity:

| Spacing d(Å) | Relative Intensity $I/I_O$ |
|---|---|
| 5.64 | 10 |
| 5.16 | 38 |
| 4.90 | 37 |
| 4.66 | 57 |
| 4.49 | 41 |

Process for Preparing Form II Tazofelone

According to another aspect, the present invention provides a process for the preparation of Form II, which comprises preparing Form I starting material by refluxing an appropriately substituted aldehyde with an appropriately substituted rhodanine in glacial acetic acid using fused sodium acetate as a catalyst then reducing the resultant thiazolidinone with a suitable reducing agent such as hydrogen and palladium on carbon. The Form I starting material is then slurried in an organic liquid, in which Form I has a solubility of at least 5% by weight at STP, by adding an amount of Form I which exceeds the solubility limit of the solvent to produce a slurry.

To speed conversion of Form I to Form II, the slurry may be agitated with an agitating device such as a mechanical or magnetic agitator or ultrasound, etc., until the conversion is substantially complete, after about 2 to 48 hours. Preferably, the slurry is agitated for 2 hours. Longer than 48 hours may be required for low purity material (purity <99%). In these cases, heating from about 20° C. to about 60° C. will also increase the conversion rate. Standard analytical techniques, such as X-ray diffraction, can be used to monitor the process in order to determine when conversion is complete.

In some cases conversion to Form II can be enhanced by isolating the crystals then reslurrying in fresh solvent. Conversion, in general, will be slower in solvents in which Tazofelone is less soluble, such as toluene. In addition, conversion can be enhanced by seeding the slurry with a small amount of Form II. Preferably, the slurry is seeded with a small amount Form II to facilitate convertion.

The process is conveniently performed at temperatures from about 20° C. to about 60° C. Ambient temperature and atmospheric pressure is preferred.

Suitable Tazofelone organic solvents include polar solvents such as methanol, ethanol, isopropanol, acetone, methyl ethyl ketone, acetonitrile, ethyl acetate, methyl acetate, isopropyl acetate or tetrahydrofuran. Other suitable solvents include non-polar solvents such as toluene, mixtures of ethyl acetate and alkane solvents such as heptane, hexane, pentane or cyclohexane; etheral solvents such as diethyl ether or tert-butyl methyl ether, or dichloromethane. Preferred solvents are toluene, ethyl acetate or heptane/ethyl acetate with the most preferred solvent being ethyl acetate.

The following Examples illustrate the invention.

EXAMPLE 1

This Example illustrates preparation of (±)-5-{[3,5-bis(1,1-dimethylethyl)-4-hydroxyphenyl]methyl}-4-thiazolidinone Form II from starting materials.

A. Preparation of Form I Starting Material

To 23.0 g (0.35 mol, 5 equiv.) of zinc dust at reflux in glacial acetic acid was added three 5 g (0.014 mol, 0.2 equiv.) portions of (±)-5-{[3,5-bis(1,1-dimethylethyl)-4-hydroxyphenyl]methyl}-2-thioxo-4-thiazolidinone at 30 minutes intervals followed by two 5 g (0.014 mol, 0.2 equiv.) portions at 60 minute intervals for a total of 25 g, 0.071 mol, 1 equiv. The resulting gray mixture was refluxed for 16 hours then cooled to 23° C. Hydrochloric acid (6 M, 178 mL) was then added dropwise over a 30 minute period under a flow of nitrogen. The resulting mixture was stirred under the flow of nitrogen for 4 hours before being vacuum filtered through a glass frit. The gray solid collected was dissolved in 300 mL of warm ethyl acetate and washed sequentially with 150 mL of 1M hydrochloric acid, 100 mL of saturated aqueous sodium bicarbonate, and 100 mL of a 1:1 mixture of brine and saturated aqueous sodium bicarbonate. The organic layer was dried over sodium sulfate and evaporated to form 21.5 g (95%) of a white solid. To 18.46 g of this material was added 46 mL of ethyl acetate and the mixture was heated to reflux.

The resulting solution was then allowed to cool and was seeded with 20 mg of Form II at 76° C., 73° C., and 70° C. After reaching 23° C., a 0.57 g sample was removed and found to be mostly Form I with some Form II present by solid-state NMR.

B. Conversion to Form II

The resulting mixture was then stirred at 40° C. for approximately 24 hours before a second 1.21 g sample was removed and found to be approximately 70% Form II and 30% Form I by solid-state NMR. The mixture was allowed to stir at 40° C. for another 24 hours before being cooled to 23° C. The solid was isolated by filtration and dried to afford 13.71 g of a white solid. Analysis by x-ray diffraction (XRD) and SSNMR indicated that 100% of the Form II polymorph was formed. The total yield including samples was 14.9 g (81%).

EXAMPLE 2

(±)-5-{[3,5-bis(1,1-dimethylethyl)-4-hydroxyphenyl] methyl}-4-thiazolidinone

Tazofelone Form I (40.24 g) was slurried in 160 mL of toluene and heated to reflux to dissolve all solids. The solution was allowed to cool slowly with stirring and at a temperature below 50° C., white solids precipitated. After one hour, the temperature had cooled to room temperature and a sample was drawn. The solids were found by SSNMR to be mainly Form I with a small amount of Form II. After stirring for 1 hour at room temperature, another aliquot was filtered and dried. This sample was also found to be a mixture of Forms I and II. Additional samples were taken after 6 hours, 22 hours, and of the final bulk of the material after 94 hours. All were found to be exclusively Form II by SSNMR and XRD. The total combined weight of all of the samples drawn was 38.5 g (95.8% recovery).

EXAMPLE 3

(±)-5-{[3,5-bis(1,1-dimethylethyl)-4-hydroxyphenyl] methyl}-4-thiazolidinone

A mixture of 75% Form I and 25% Form II (14.00 g) was slurried in 28 mL of ethyl acetate. After stirring for 5 hours, a 2 mL aliquot was filtered and dried. Another sample was taken after 24 hours. After 48 hours, the slurry was cooled in an ice water bath. The resulting slurry was filtered through coarse glass and the solids were washed with 14 mL of cold 1:1 ethyl acetate: heptane. After drying in a vacuum oven, 13.1 g of white crystals was collected from the combined samples (94.0% recovery). Solid-state NMR and XRD indicated that both the 5 hour sample and the 24 hour sample were already exclusively polymorph Form II.

Pharmaceutically Acceptable Salts

Pharmaceutically acceptable salts are considered to be encompassed within the compounds and method of the present invention. The term "pharmaceutically acceptable salts" refers to salts of substantially pure Form II which are substantially non-toxic to living organisms (e.g., Na, K, Ca, Mg).

Typical pharmaceutically acceptable salts include those salts prepared by reactions of Form II with a pharmaceutically acceptable alkali metal or organic base depending on the types of substituents present.

It should be recognized that any particular cation forming a part of any salt of this invention is not critical, so long as the salt, as a whole, is pharmacologically acceptable and as long as the cation moiety does not contribute undesired qualities.

The present invention provides a new substantially pure crystal form of Tazofelone. Accordingly, the present invention is also directed to pharmaceutical compositions which include Tazofelone Form II in association with one or more pharmaceutically acceptable diluents, excipients or carriers.

In making the pharmaceutical compositions of the present invention, Form II will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The following formulation examples employ as active ingredient Form II. The examples are illustrative only and are not intended to limit the scope of the invention in any way.

EXAMPLE 4

Hard gelatin capsules are prepared using the following ingredients:

|  | Quantity (mg/tablet) |
| --- | --- |
| Tazofelone Form II | 250 |
| Starch dried | 200 |
| Magnesium stearate | 10 |

The above ingredients are mixed and filled into hard gelatin capsules in 460 mg quantities.

EXAMPLE 5

A tablet formula is prepared using the ingredients below:

|  | Quantity (mg/tablet) |
|---|---|
| Tazofelone Form II | 250 |
| Cellulose, microcrystalline | 400 |
| Silicon dioxide, fumed | 10 |
| Stearic Acid | 5 |

The components are blended and compressed to form tablets each weighing 665 mg.

EXAMPLE 6

An aerosol solution is prepared containing the following components:

|  | Weight % |
|---|---|
| Tazofelone Form II | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 7

Tablets each containing 60 mg of active ingredient are made up as follows:

| Tazofelone Form II | 60.0 mg |
|---|---|
| Starch | 45.0 mg |
| Microcrystalline Cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 8

Capsules each containing 80 mg of medicament are made as follows:

|  | Quantity (mg/capsule) |
|---|---|
| Tazofelone Form II | 80 mg |
| Starch | 59 mg |
| Microcrystalline Cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 9

Suppositories each containing 225 mg of active ingredient are made as follows:

|  | Quantity (mg/suppository) |
|---|---|
| Tazofelone Form II | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 10

Suspensions each containing 50 mg of medicament per 5 ml dose are made as follows:

|  | Quantity |
|---|---|
| Tazofelone Form II | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5.0 ml |

The medicament is passed through a No. 45 mesh U.S., sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 11

Capsules each containing 150 mg of medicament are made as follows:

|  | Quantity (mg/capsule) |
|---|---|
| Tazofelone Form II | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

Method of Treating Inflammation

Tazofelone is known to be useful in treating and/or preventing inflammation, IBD, allergies, arthritis, hypoglycemia and muscular dystrophy and in preventing ischemia induced cell damage. The term IBD as used for the purposes of the present invention means any disorder of the digestive system which is characterized by inflammation. Examples of such disorders may include ulcerative colitis and Chrohn's disease. According to yet another aspect, therefore, the present invention provides a method of preventing or treating inflammation, IBD, allergies, arthritis, hypoglycemia and muscular dystrophy in a mammal suffering from or susceptible to such disease comprising administering a therapeutically effective amount of substantially pure Form II.

Tazofelone is effective over a wide dosage range in treating IBD. Thus, as used herein, the term "therapeutically effective amount" refers to an amount capable of diminishing the adverse symptoms of a particular disease. Preferred dosage is in the range of from about 0.001 to about 200 mg/kg of body weight/day. In the treatment of adult humans, the range of about 50 mg/kg in single or divided doses is particularly preferred. However, the particular dose of compound administered according to this invention will of course be determined by the particular circumstances surrounding the case, including the age, weight and response of the individual patient, the severity of the patient's symptoms, the route of administration, and similar considerations. Therefore, the above dosage ranges are not intended to limit the scope in any way.

While substantially pure Form II is preferably administered orally or intrarectally, it may also be administered by a variety of other routes such as the transdermal, subcutaneous, intranasal, intramuscular and intravenous routes.

We claim:

1. A substantially pure Form II (±)-5-{[3,5-bis(1,1-dimethylethyl)-4-hydroxyphenyl]methyl}-4-thiazolidinone having the following x-ray diffraction data obtained with a CuKα radiation of $\lambda=1.53056$ Å:

| Spacing d: Å | Relative intensities $I/I_o$ |
|---|---|
| 5.64 | 10 |
| 5.16 | 38 |
| 4.90 | 37 |
| 4.66 | 57 |
| 4.49 | 41. |

2. A process for preparing and isolating substantially pure Form II (±)-5-{[3,5-bis(1,1-dimethylethyl)-4-hydroxyphenyl]methyl}-4-thiazolidinone which comprises slurrying Form I in an organic solvent.

3. A process according to claim 2 in which Form II (±)-5-{[3,5-bis(1,1-dimethylethyl)-4-hydroxyphenyl]methyl}-4-thiazolidinone is slurried in an organic solvent.

4. A process according to claim 2 or 3 wherein the organic solvent is ethyl acetate, toluene or 1:1 heptane/ethyl acetate.

5. A process according to claim 4 wherein the slurry is agitated.

6. A process according to claim 5 further comprising slurrying Form II at ambient temperature.

7. A pharmaceutical formulation adapted for treating inflammatory bowel disease comprising as the active ingredient substantially pure Form II (±)-5-{[3,5-bis(1,1-dimethylethyl)-4-hydroxyphenyl]methyl}-4-thiazolidinone having an x-ray diffraction pattern with d spacings at 5.64 Å, 5.16 Å, 4.90 Å, 4.66 Å and 4.49 Å or a pharmaceutically acceptable salt thereof, in association with one or more pharmaceutically acceptable diluents, excipients or carriers thereof.

8. Substantially pure Form II (±)-5-{[3,5-bis(1,1-dimethylethyl)-4-hydroxyphenyl]methyl}-4-thiazolidinone for use as a pharmaceutical.

9. A method of preventing or treating inflammatory bowel disease in a mammal suffering from or susceptible to such disease comprising administering a therapeutically effective amount of substantially pure Form II (±)-5-{[3,5-bis(1,1-dimethylethyl)-4-hydroxyphenyl]methyl}-4-thiazolidinone.

* * * * *